(12) United States Patent
McIntosh et al.

(10) Patent No.: US 12,637,709 B2

(45) Date of Patent: May 26, 2026

(54) METHOD FOR DETECTING SARS-COV-RELATED BETACORONAVIRUSES

(71) Applicant: UNIVERSITY OF FLORIDA RESEARCH FOUNDATION, INCORPORATED, Gainesville, FL (US)

(72) Inventors: Michael McIntosh, Gainesville, FL (US); Ibukun A. Akinyemi, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 918 days.

(21) Appl. No.: 17/811,224

(22) Filed: Jul. 7, 2022

(65) Prior Publication Data

US 2023/0042039 A1 Feb. 9, 2023

Related U.S. Application Data

(60) Provisional application No. 63/219,076, filed on Jul. 7, 2021.

(51) Int. Cl.
*C12Q 1/6853* (2018.01)
*C12Q 1/686* (2018.01)

(52) U.S. Cl.
CPC ........... *C12Q 1/6853* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 6,410,278 | B1 | 6/2002 | Notomi et al. |
| 6,974,670 | B2 | 12/2005 | Notomi et al. |
| 7,494,790 | B2 | 2/2009 | Notomi et al. |
| 8,017,357 | B2 | 9/2011 | Notomi et al. |
| 8,557,523 | B2 | 10/2013 | Yonekawa et al. |
| 9,909,168 | B2 | 3/2018 | Notomi et al. |
| 2007/0099178 | A1 | 5/2007 | Minekawa et al. |
| 2009/0092962 | A1 | 4/2009 | Minekawa et al. |
| 2009/0117537 | A1 | 5/2009 | Minekawa et al. |

OTHER PUBLICATIONS

"Detection of 2019 Novel Coronavirus (2019-nCOV) in Suspected Human Cases by RT-PCR," *HKU Med LKS Faculty of Medicine School of Public Health*, pp. 1-5, Jan. 16, 2020.

"SARS-CoV-2 Rapid Colorimetric LAMP Assay Kit, Catalog # NEB: E2019S," *New England Biolabs, Inc.*, Version 2.0, pp. 1-8, Nov. 2021, available online at https://www.neb.com/products/e2019-sars-cov-2-rapid-colorimetric-lamp-assay-kit#Product%20Information.

Butt, Zaeem Mehmood et al. "Development of a Dual-Gene Loop-Mediated Isothermal Amplification (LAMP) Detection Assay for SARS-CoV-2: A Preliminary Study," *MedRxiv*, Preprint, Apr. 11, 2020, (11 pages), DOI: 10.1101/2020.04.08.20056986.

Chu, Daniel K.W. et al. "Molecular Diagnosis of a Novel Coronavirus (2019-nCoV) Causing an Outbreak of Pneumonia," Clinical Chemistry, vol. 66, No. 4, pp. 549-555, Apr. 2020 (ePub: Jan. 31, 2020), DOI: 10.1093/clinchem/hvaa029.

Corman, Victor et al. "Diagnostic Detection of 2019-nCOV by Real-Time RT-PCR," *World Health Organization*, vol. 17, pp. 1-13, Jan. 17, 2020, available online: https://www.who.int/docs/default-source/coronaviruse/protocol-v2-1.pdf.

Ganguli, Anurup et al. "Rapid Isothermal Amplification and Portable Detection System for SARS-CoV-2," *Proceedings of the National Academy of Sciences*, vol. 117, No. 37, pp. 22727-22735, Sep. 15, 2020, available online: https://www.pnas.org/doi/pdf/10.1073/pnas.2014739117.

Huang, Wei E. et al. "RT-LAMP for Rapid Diagnosis of Coronavirus SARS-CoV-2," *Microbial Biotechnology*, vol. 13, Issue 4, (12 pages), Apr. 25, 2020, DOI: 10.1111/1751-7915.13586.

Lalli, Matthew A. et al. "Rapid and Extraction-Free Detection of SARS-CoV-2 From Saliva With Colorimetric LAMP," *MedRxiv*, Preprint, (25 pages), May 11, 2020, DOI: 10.1101/2020.05.07.20093542.

Loeffelholz, Michael J. et al. "Laboratory Diagnosis of Emerging Human Coronavirus Infections—The State of the Art," *Emerging Microbes & Infections*, vol. 9, No. 1, pp. 747-756, Mar. 17, 2020, DOI: 10.1080/22221751.2020.1745095.

Lu, Renfei et al. "A Novel Reverse Transcription Loop-Mediated Isothermal Amplification Method for Rapid Detection of SARS-CoV-2," *International Journal of Molecular Sciences*, vol. 21, No. 8:2826, pp. 1-10, Apr. 18, 2020, DOI: 10.3390/ijms21082826.

Rabe, Brian A. et al. "SARS-Cov-2 Detection Using an Isothermal Amplification Reaction and a Rapid, Inexpensive Protocol for Sample Inactivation and Purification," *Proceedings of the National Academy of Sciences*, vol. 117, No. 39, pp. 244450-24458, Sep. 29, 2020, DOI: 10.1073/pnas.2011221117.

Zhang, Yinhua et al. "Enhancing Colorimetric Loop-Mediated Isothermal Amplification Speed and Sensitivity With Guanidine Chloride," *BioTechniques*, vol. 69, No. 3, pp. 179-185, Jun. 16, 2020, (ePub: Jul. 8, 2020), DOI: 10.2144/btn-2020-0078.

Zhang, Yinhua et al. "Rapid Molecular Detection of SARS-CoV-2 (COVID-19) Virus RNA Using Colorimetric LAMP," *MedRxiv*, Preprint, Feb. 29, 2020, (14 pages), DOI: 10.1101/2020.02.26.20028373.

*Primary Examiner* — Young J Kim

(74) *Attorney, Agent, or Firm* — Alston & Bird LLP

(57) ABSTRACT

Described are oligonucleotides (LAMP primers), compositions, kits, and method for loop-mediated-isothermal amplification (LAMP) and/or detection of SARS-CoV-related betacoronaviruses. The methods can be used to in diagnosing SARS-CoV-2 infection.

18 Claims, 3 Drawing Sheets

Specification includes a Sequence Listing.

SEQUENCE LISTING

Sequence total quantity: 36
SEQ ID NO: 1              moltype = DNA   length = 29
FEATURE                   Location/Qualifiers
source                    1..29
                          mol_type = other DNA
                          organism = synthetic construct
SEQUENCE: 1
gaacatgtsc aaatwcacac aatcgacgg                                        29

SEQ ID NO: 2              moltype = DNA   length = 29
FEATURE                   Location/Qualifiers
source                    1..29
                          mol_type = other DNA
                          organism = synthetic construct
SEQUENCE: 2
gaacatgtsc aaatacacac aatcgacgg                                        29

SEQ ID NO: 3              moltype = DNA   length = 29
FEATURE                   Location/Qualifiers
source                    1..29
                          mol_type = other DNA
                          organism = synthetic construct
SEQUENCE: 3
gaacatgtsc aaattcacac aatcgacgg                                        29

SEQ ID NO: 4              moltype = DNA   length = 29
FEATURE                   Location/Qualifiers
source                    1..29
                          mol_type = other DNA
                          organism = synthetic construct
SEQUENCE: 4
gaacatgtcc aaatwcacac aatcgacgg                                        29

SEQ ID NO: 5              moltype = DNA   length = 29
FEATURE                   Location/Qualifiers
source                    1..29
                          mol_type = other DNA
                          organism = synthetic construct
SEQUENCE: 5
gaacatgtgc aaatwcacac aatcgacgg                                        29

SEQ ID NO: 6              moltype = DNA   length = 29
FEATURE                   Location/Qualifiers
source                    1..29
                          mol_type = other DNA
                          organism = synthetic construct
SEQUENCE: 6
gaacatgtgc aaatacacac aatcgacgg                                        29

SEQ ID NO: 7              moltype = DNA   length = 29
FEATURE                   Location/Qualifiers
source                    1..29
                          mol_type = other DNA
                          organism = synthetic construct
SEQUENCE: 7
gaacatgtgc aaattcacac aatcgacgg                                        29

SEQ ID NO: 8              moltype = DNA   length = 29
FEATURE                   Location/Qualifiers
source                    1..29
                          mol_type = other DNA
                          organism = synthetic construct
SEQUENCE: 8
gaacatgtcc aaattcacac aatcgacgg                                        29

SEQ ID NO: 9              moltype = DNA   length = 29
FEATURE                   Location/Qualifiers
source                    1..29
                          mol_type = other DNA
                          organism = synthetic construct
SEQUENCE: 9
gaacatgtcc aaatacacac aatcgacgg                                        29

SEQ ID NO: 10             moltype = DNA   length = 74
FEATURE                   Location/Qualifiers
source                    1..74
                          mol_type = other DNA
                          organism = synthetic construct -continued

```
SEQUENCE: 10
tcttccgaaa cgaatgagta cataagttcg tactcaggag ttgwtaatcc agtaatggwa   60
ccaatttatg atga                                                     74

SEQ ID NO: 11              moltype = DNA   length = 74
FEATURE                    Location/Qualifiers
source                     1..74
                           mol_type = other DNA
                           organism = synthetic construct
SEQUENCE: 11
tcttccgaaa cgaatgagta cataagttcg tactcaggag ttgwtaatcc agtaatggaa   60
ccaatttatg atga                                                     74

SEQ ID NO: 12              moltype = DNA   length = 74
FEATURE                    Location/Qualifiers
source                     1..74
                           mol_type = other DNA
                           organism = synthetic construct
SEQUENCE: 12
tcttccgaaa cgaatgagta cataagttcg tactcaggag ttgwtaatcc agtaatggta   60
ccaatttatg atga                                                     74

SEQ ID NO: 13              moltype = DNA   length = 74
FEATURE                    Location/Qualifiers
source                     1..74
                           mol_type = other DNA
                           organism = synthetic construct
SEQUENCE: 13
tcttccgaaa cgaatgagta cataagttcg tactcaggag ttgataatcc agtaatggwa   60
ccaatttatg atga                                                     74

SEQ ID NO: 14              moltype = DNA   length = 74
FEATURE                    Location/Qualifiers
source                     1..74
                           mol_type = other DNA
                           organism = synthetic construct
SEQUENCE: 14
tcttccgaaa cgaatgagta cataagttcg tactcaggag ttgttaatcc agtaatggwa   60
ccaatttatg atga                                                     74

SEQ ID NO: 15              moltype = DNA   length = 74
FEATURE                    Location/Qualifiers
source                     1..74
                           mol_type = other DNA
                           organism = synthetic construct
SEQUENCE: 15
tcttccgaaa cgaatgagta cataagttcg tactcaggag ttgataatcc agtaatggaa   60
ccaatttatg atga                                                     74

SEQ ID NO: 16              moltype = DNA   length = 74
FEATURE                    Location/Qualifiers
source                     1..74
                           mol_type = other DNA
                           organism = synthetic construct
SEQUENCE: 16
tcttccgaaa cgaatgagta cataagttcg tactcaggag ttgataatcc agtaatggta   60
ccaatttatg atga                                                     74

SEQ ID NO: 17              moltype = DNA   length = 74
FEATURE                    Location/Qualifiers
source                     1..74
                           mol_type = other DNA
                           organism = synthetic construct
SEQUENCE: 17
tcttccgaaa cgaatgagta cataagttcg tactcaggag ttgttaatcc agtaatggta   60
ccaatttatg atga                                                     74

SEQ ID NO: 18              moltype = DNA   length = 74
FEATURE                    Location/Qualifiers
source                     1..74
                           mol_type = other DNA
                           organism = synthetic construct
SEQUENCE: 18
tcttccgaaa cgaatgagta cataagttcg tactcaggag ttgttaatcc agtaatggta   60
ccaatttatg atga                                                     74

SEQ ID NO: 19              moltype = DNA   length = 37
FEATURE                    Location/Qualifiers
source                     1..37
```

-continued

```
                        mol_type = other DNA
                        organism = synthetic construct
SEQUENCE: 19
cttgtgctta caaaggcacg ctagtagtcg tcgtcgg                                    37

SEQ ID NO: 20             moltype = DNA   length = 32
FEATURE                   Location/Qualifiers
source                    1..32
                          mol_type = other DNA
                          organism = synthetic construct
SEQUENCE: 20
ttagttcgtt tagaccagaa gatcaggaac tc                                         32

SEQ ID NO: 21             moltype = DNA   length = 68
FEATURE                   Location/Qualifiers
source                    1..68
                          mol_type = other DNA
                          organism = synthetic construct
SEQUENCE: 21
acagctacgt taatagttaa tagcgtactt cttttactca cgttaccaat attgcagcag         60
tacgcaca                                                                    68

SEQ ID NO: 22             moltype = DNA   length = 26
FEATURE                   Location/Qualifiers
source                    1..26
                          mol_type = other DNA
                          organism = synthetic construct
SEQUENCE: 22
acactagcca tccttactgc gcttcg                                                26

SEQ ID NO: 23             moltype = DNA   length = 366
FEATURE                   Location/Qualifiers
source                    1..366
                          mol_type = genomic DNA
                          organism = SARS-CoV-2
SEQUENCE: 23
gaacatgtcc aaattcacac aatcgacggt tcatccggag ttgttaatcc agtaatggaa         60
ccaatttatg atgaaccgac gacgactact agcgtgcctt tgtaagcaca agctgatgag        120
tacgaactta tgtactcatt cgtttcggaa gagacaggta cgttaatagt taatagcgta        180
cttctttttc ttgctttcgt ggtattcttg ctagttacac tagccatcct tactgcgctt        240
cgattgtgtg cgtactgctg caatattgtt aacgtgagtc ttgtaaaacc ttcttttttac        300
gtttactctc gtgttaaaaa tctgaattct tctagagttc ctgatcttct ggtctaaacg        360
aactaa                                                                    366

SEQ ID NO: 24             moltype = DNA   length = 360
FEATURE                   Location/Qualifiers
source                    1..360
                          mol_type = genomic DNA
                          organism = SARS-CoV
SEQUENCE: 24
ccgaatgtgc aaatacacac aatcgacggc tcttcaggag ttgctaatcc agcaatggat         60
ccaatttatg atgagccgac gacgactact agcgtgcctt tgtaagcaca agaaagtgag        120
tacgaactta tgtactcatt cgtttcggaa gaaacaggta cgttaatagt taatagcgta        180
cttctttttc ttgctttcgt ggtattcttg ctagtcacac tagccatcct tactgcgctt        240
cgattgtgtg cgtactgctg caatattgtt aacgtgagtt agtaaaaacc aacggtttac        300
gtctactcgc gtgttaaaaa tctgaactct tctgaaggag ttcctgatct tctggtctaa        360

SEQ ID NO: 25             moltype = DNA   length = 25
FEATURE                   Location/Qualifiers
source                    1..25
                          mol_type = other DNA
                          organism = synthetic construct
SEQUENCE: 25
atgtctggta aaggccaaca acaac                                                25

SEQ ID NO: 26             moltype = DNA   length = 60
FEATURE                   Location/Qualifiers
source                    1..60
                          mol_type = other DNA
                          organism = synthetic construct
SEQUENCE: 26
tttccttggg tttgttctgg accacgtcta aggccaaact gtcactaaga aatctgctgc         60

SEQ ID NO: 27             moltype = DNA   length = 23
FEATURE                   Location/Qualifiers
source                    1..23
                          mol_type = other DNA
                          organism = synthetic construct
SEQUENCE: 27
```

-continued

```
gcagtacgtt tttgccgagg ctt                                          23

SEQ ID NO: 28          moltype = DNA   length = 31
FEATURE                Location/Qualifiers
source                 1..31
                       mol_type = other DNA
                       organism = synthetic construct
SEQUENCE: 28
tgatctttga aatttggatc tttgtcatcc a                                 31

SEQ ID NO: 29          moltype = DNA   length = 57
FEATURE                Location/Qualifiers
source                 1..57
                       mol_type = other DNA
                       organism = synthetic construct
SEQUENCE: 29
taatcagaca aggaactgat tacaagttcc cgaaggtgtg acttccatgc caatgcg     57

SEQ ID NO: 30          moltype = DNA   length = 24
FEATURE                Location/Qualifiers
source                 1..24
                       mol_type = other DNA
                       organism = synthetic construct
SEQUENCE: 30
acattggccg caaattgcac aatt                                         24

SEQ ID NO: 31          moltype = DNA   length = 24
FEATURE                Location/Qualifiers
source                 1..24
                       mol_type = other DNA
                       organism = synthetic construct
SEQUENCE: 31
gaccacacaa ggcagatggg ctat                                         24

SEQ ID NO: 32          moltype = DNA   length = 60
FEATURE                Location/Qualifiers
source                 1..60
                       mol_type = other DNA
                       organism = synthetic construct
SEQUENCE: 32
gttaactaca tctacttgtg ctatgtagtt ataaacgttt tcgcttttcc gtttacgata  60

SEQ ID NO: 33          moltype = DNA   length = 31
FEATURE                Location/Qualifiers
source                 1..31
                       mol_type = other DNA
                       organism = synthetic construct
SEQUENCE: 33
cgagaattca ttctgcacaa gagtagacta t                                 31

SEQ ID NO: 34          moltype = DNA   length = 28
FEATURE                Location/Qualifiers
source                 1..28
                       mol_type = other DNA
                       organism = synthetic construct
SEQUENCE: 34
ttacacatta gggctcttcc atataggc                                     28

SEQ ID NO: 35          moltype = DNA   length = 65
FEATURE                Location/Qualifiers
source                 1..65
                       mol_type = other DNA
                       organism = synthetic construct
SEQUENCE: 35
tcacatagca atctttaatc agtgtgtaac attaggtaca ctcgatcgta ctccgcgtgg  60
cctcg                                                              65

SEQ ID NO: 36          moltype = DNA   length = 23
FEATURE                Location/Qualifiers
source                 1..23
                       mol_type = other DNA
                       organism = synthetic construct
SEQUENCE: 36
ggaggacttg aaagagccac cac                                          23
```

METHOD FOR DETECTING SARS-COV-RELATED BETACORONAVIRUSES

CROSS-REFERENCE TO RELATED APPLICATIONS

This application claims the benefit of U.S. Provisional Application No. 63/219,076, filed Jul. 7, 2021, which is incorporated herein by reference.

SEQUENCE LISTING

The Sequence Listing written in file T18249US003_SeqListing.xml is 34 kilobytes in size, was created Jul. 7, 2022, and is hereby incorporated by reference

INTRODUCTION

Point-of-care diagnostic tests (POCTs) play a vital role in identifying infected and virus shedding individuals rapidly to better inform decisions on quarantine, isolation, and treatment. Current COVID-19/SARS-CoV-2 detection tests depend on complex and expensive real time RT-PCR platforms requiring centralized laboratories for sample processing and testing, specialized expertise, and expensive equipment. These factors contribute to high costs, limited access, and delay in receiving results.

An alternative to RT-PCR detection of nucleic acid is loop-mediated-isothermal amplification (LAMP). LAMP was developed by Notomi, et al., 2000 ("Loop-mediated isothermal amplification of DNA." Nucleic Acids Res 28, E63). LAMP utilizes a strand displacing DNA polymerase and 4 to 6 primers targeting 6-8 regions of a target nucleic acid sequence. Polymerization from the primers leads to stem-loop formation at the ends of nascent amplified DNA that permits additional priming and concatemeric amplification of DNA at a single temperature.

To address the need for rapid actionable test results, and to provide COVID-19/SARS-CoV-2 testing to resource limited regions, a coronavirus POCT that can detect SARS-CoV-2 is needed.

SUMMARY

Described are oligonucleotides (LAMP primers), compositions, and kits for loop-mediated isothermal amplification (LAMP) and/or detection of SARS-CoV-related betacoronaviruses. In some embodiments, LAMP primers, compositions, and kits for amplification of a region of coronaviruses conserved among closely related SARS-CoV-related betacoronaviruses, included SRAS-CoV-2 are described. The described LAMP primers, compositions, and kits can be used to detect 2003 SARS-CoV or 2019 SARS-CoV-2. The LAMP primers, compositions, and kits are also expected to be able to amplify and detect other bat origin betacoronaviruses of future zoonotic and pandemic potential.

Described are kits for rapid colorimetric in vitro detection of SARS-CoV-related betacoronavirus. In some embodiments, detection of SARS-CoV-related betacoronaviruses in a sample is indicated by a visual endpoint. In some embodiments, the LAMP primers, compositions, and kits can be used to detection of SARS-CoV-related betacoronaviruses in a sample in real time. The described kits can be used as point-of-care (POCT) diagnostics for rapid detection of SARS-CoV-related betacoronaviruses.

In some embodiments, the described LAMP primers, compositions, and kits can be used to detect a SARS-CoV-related betacoronavirus in a sample from a subject. The sample can be, but is not limited to, a nasal or throat swab; saliva, blood or fecal sample; or in vitro culture sample.

Described are methods of using the LAMP primers, compositions, and kits to amplify and or detect SARS-CoV-related betacoronavirus target nucleic acid sequence in a sample. The methods can be used to assist in diagnosing SARS-CoV-2 infection.

DESCRIPTION

Figure 1:
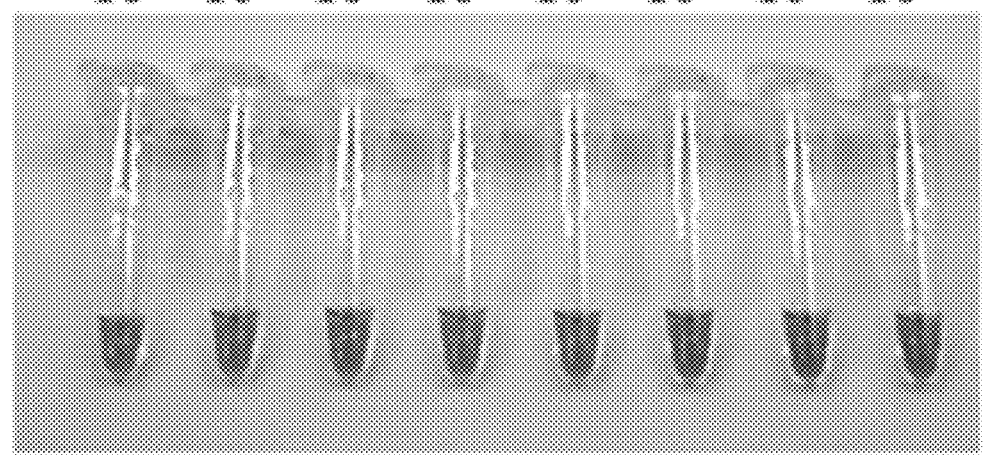
FIG. 1. Comparison of detection results for capripoxvirus POCT using qPCR and LAMP assays. Hydroxynaphthol blue (HNB) reveals LAMP results as positive (sky blue) or negative (violet).

Before describing the present teachings in detail, it is to be understood that the disclosure is not limited to specific compositions or process steps, as such may vary. It should be noted that, as used in this specification and the appended claims, the singular form "a," "an," and "the" include plural references unless the context clearly dictates otherwise. Thus, for example, reference to "an oligomer" includes a plurality of oligomers and the like. The conjunction "or" is to be interpreted in the inclusive sense, i.e., as equivalent to "and/or," unless the inclusive sense would be unreasonable in the context.

In general, the term "about" indicates insubstantial variation in a quantity of a component of a composition not having any significant effect on the activity or stability of the composition. When the specification discloses a specific value for a parameter, the specification should be understood as alternatively disclosing the parameter at "about" that value. All ranges are to be interpreted as encompassing the endpoints in the absence of express exclusions such as "not including the endpoints"; thus, for example, "within 10-15" includes the values 10 and 15. Also, the use of "comprise," "comprises," "comprising," "contain," "contains," "containing," "include," "includes," and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components. Embodiments in the specification that recite "consisting essentially of" various components are also contemplated as "consisting of". "Consisting essentially of" means that additional component(s), composition(s) or method step(s) that do not materially change the basic and novel characteristics of the compositions and methods described herein may be included in those compositions or methods.

A "nucleic acid" includes both RNA and DNA. RNA and DNA include, but are not limited to, cDNA, genomic DNA, viral DNA, plasmid DNA, viral RNA, synthetic RNA or DNA, and mRNA. Nucleic acid also includes modified RNA or DNA. Nucleic acid may refer to that which is purified by a method separate from the described LAMP assay or may be detected directly from the sample in the described LAMP assay with or without integrated minimal sample preparation procedures such as heat or detergent denaturing and or or magnetic bead extraction of RNA and or DNA.

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters or by inspection and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity. Unless otherwise indicated the window of comparison between two sequences is defined by the entire length of the shorter of the two sequences.

A "primer" is an oligonucleotide that hybridizes to a target nucleic acid, or its complement, and participates in a nucleic acid amplification reaction. A primer hybridizes to a template nucleic acid and has a 3' end that can be extended by polymerization. In some embodiments, primers contain at least about 10 contiguous bases, and optionally at least 18, 19, 20, 21, 22, 23, 24, 25, 26, 27, 28, 29, or 30 contiguous bases, that are complementary to a region of the target nucleic acid sequence or its complementary strand. The contiguous bases may be at least about 80%, at least about 90%, at least 95%, or completely complementary to the target sequence to which the primer oligonucleotide binds. Primers optionally may include modified nucleotides and/or degenerate positions.

"Hybridization" or "hybridize" indicate meant the ability of two completely or partially complementary nucleic acid strands to come together under specified hybridization assay conditions in a parallel or antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art.

An "amplification product" or amplicon is a nucleic acid molecule generated in a nucleic acid amplification reaction and which is derived from a target nucleic acid. An amplicon or amplification product contains a target nucleic acid sequence that may be of the same or opposite sense as a target nucleic acid.

"Loop-mediated amplification" (LAMP) is a method of amplifying double- or single-stranded DNA or RNA template at elevated temperature using two or three pairs of primers recognizing six or eight distinct sequences in the target nucleic acid (Notomi et al. "Loop-mediated isothermal amplification (LAMP): principle, features, and future prospects." J Microbiol 2015 53(1):1-5).

A "sample" includes any specimen containing or suspected of containing SARS-CoV-related betacoronavirus or a SARS-CoV-related betacoronavirus target nucleic acid. A "sample" may contain or may be suspected of containing SARS-CoV-related betacoronavirus or components thereof, such as nucleic acids or fragments of nucleic acids. A sample may be a complex mixture of components. Samples include biological samples which include any tissue or material derived from a living or dead mammal or organism, including, e.g., nasopharyngeal (NP) swab, oropharyngeal (OP) swab, nasal mid-turbinate swab, nasal (anterior nares) swab, nasopharyngeal wash/aspirate, nasal wash/aspirate, saliva specimen, throat swab, blood, plasma, serum, mucous specimen, biopsy, or combinations thereof. A sample may be treated to physically or mechanically disrupt tissue or cell structure to release intracellular nucleic acids into a solution which may contain enzymes, buffers, salts, detergents and the like, to prepare the sample for analysis.

A "SARS-CoV-related betacoronavirus" is that which is considered highly similar to or phylogenetically similar to 2003 SARS-CoV or 2019 SARS-CoV-2. Taxonomically, the target classifications of SARS-CoV-related betacoronaviruses may be referred to as Lineage B and subgenus Sarbecovirus and Lineage D, subgenus Nobecovirus. The test is not designed to detect other more distantly related human betacoronaviruses such as Lineage A, subgenus Embecovirus that includes common human coronaviruses OC43 and HKU1 of lower pathogenicity in humans, or Lineage C, subgenus Merbecovirus that includes the highly pathogenic Middle East respiratory syndrome coronavirus. Bats are common carriers of diverse virus genera. The described oligonucleotides and kits amplify and detect those bat coronaviruses that are closely related to 2003 SARS-CoV and 2019 SARS-CoV-2. As such the described oligonucleotides and kits are expected to amplify and detect existing COVID-19 viruses as they further diverge in humans as well as newly identified emerging SARS-like coronaviruses of zoonotic and pandemic potential.

I. LAMP Amplification of SARS-CoV-Related Betacoronavirus

The present disclosure provides oligonucleotides, compositions, and kits useful for amplifying, detecting, and/or quantifying SARS-CoV-related betacoronavirus target nucleic acid. The oligonucleotides, compositions, and kits can be used to determine the presence or absence of SARS-CoV-related betacoronavirus or a SARS-CoV-related betacoronavirus target nucleic acid or fragment thereof in a sample. The SARS-CoV-related betacoronavirus can be SARS-CoV, SARS-CoV-2, BtRs-BetaCoV/YN2018C coronavirus, bat coronavirus isolate Anlong-112, bat coronavirus isolate Jiyuan-84, or related betacoronaviruses. In some embodiments, the SARS-CoV-related betacoronavirus is SARS-CoV-2 or a variant thereof.

The described oligonucleotides comprise primers (LAMP primers) effective for loop-mediated amplification (LAMP) of SARS-CoV-related betacoronavirus target nucleic acid. The LAMP primers can be used in sets of four primers or sets of six primers. In some embodiments, a LAMP primer set comprises four primers. The four primers comprise a forward outer (F3) primer, a backward outer (B3) primer, a forward inner (FIP) primer, and a backward inner (BIP) primer; and recognize six distinct sequences on the SARS-CoV-related betacoronavirus target nucleic acid. In some embodiments, a LAMP primer set comprises six primers. The six primers comprise a F3 primer, a B3 primer, a FIP primer, and a BIP primer, a forward loop (FL) primer, and a backward loop (BL) primer; and recognize eight distinct sequences on the SARS-CoV-related betacoronavirus target nucleic acid.

SARS-CoV-2 detection tests and methods that utilize highly specific primer binding sites in SARS-CoV-2 are susceptible to false negative results due to the emergence of SARS-CoV-2 variants. In contrast to SARS-CoV-2 detection tests and methods that utilize highly specific primer binding sites, the described SARS-CoV-related betacoronavirus detection oligonucleotides (LAMP primer sets), compositions, and kits target conserved regions shared among closely related but divergent viruses. The described compositions and methods are capable of detecting SARS-CoV-2 variants that can arise during an ongoing pandemic.

In some embodiments, a SARS-CoV-related betacoronavirus target nucleic acid corresponds to the ORF3a-E region (region spanning ORF3a and E genes) of the SARS-CoV-2 acid sequence. In some embodiments, the target region corresponds to positions 26,116 to 26,481 of GenBank Wuhan-Hu-1 NC_045512.2 SE ID NO: 23):

```
gaacatgtccaaattcacacaatcgacggttcatccggagttgttaatcc agtaatggaaccaatttatgatgaaccgacgacgactactagcgtgcctt tgtaagcacaagctgatgagtacgaacttatgtactcattcgtttcggaa gagacaggtacgttaatagttaatagcgtacttctttttcttgctttcgt ggtattcttgctagttacactagccatccttactgcgcttcgattgtgtg cgtactgctgcaatattgttaacgtgagtcttgtaaaaccttctttttac gtttactctcgtgttaaaaatctgaattcttctagagttcctgatcttct ggtctaaacgaactaa.
```

The SARS-CoV sequence corresponding to SEQ ID NO: 23 is:

```
                                    (SEQ ID NO: 24)
aatcgacggctcttcaggagttgctaatccagcaatggatccaatttat gatgagccgacgacgactactagcgtgcctttgtaagcacaagaaagtg agtacgaacttatgtactcattcgtttcggaagaaacaggtacgttaat agttaatagcgtacttctttttcttgctttcgtggtattcttgctagtc acactagccatccttactgcgcttcgattgtgtgcgtactgctgcaata ttgttaacgtgagtttagtaaaaccaacggtttacgtctactcgcgtgt taaaaatctgaactcttctgaaggagttcctgatcttctggtctaaccg aatgtgcaaatacacac
```

II. LAMP Primers

In some embodiments, the F3 primer comprises a target hybridizing region that hybridizes to at least 15 contiguous nucleotides present in a target nucleic acid sequence corresponding to positions 1-29 of SEQ ID NO: 23 or a complement thereof. In some embodiments, a F3 primer comprises a target hybridizing region that is at least 80%, at least 85%, at least 90%, at least 95%, or 100% complementary to a target nucleic acid sequence corresponding to positions 1-29 of SEQ ID NO: 23 or a complement thereof. In some embodiments, a F3 primer comprises a nucleic acid sequence having at least 80%, at least 85%, at least 90%, at least 95%, or 100% identify to the nucleic acid sequence of any of SEQ ID NOs: 1-9. In some embodiments, a F3 primer comprises a nucleic acid sequence differing by no more than 1, 2, or 3 nucleotides from the nucleic acid sequence of any of SEQ ID NOs: 1-9. In some embodiments, a F3 primer comprises the nucleic acid sequence of any of SEQ ID NOs: 1-9. In some embodiments, a F3 primer consists of any of SEQ ID NOs: 1-9. The F3 primer is able to hybridize to a target nucleic acid or amplicon thereof and initiate nucleic acid polymerization. In some embodiments, the F3 primer hybridizes to a region of a complement of SEQ ID NO: 23.

In some embodiments, a FIP primer comprises a first target hybridizing region that hybridizes to at least 15 contiguous nucleotides present in a target nucleic acid sequence corresponding to positions 37-74 of SEQ ID NO: 23 or a complement thereof. In some embodiments, a FIP primer comprises a first target hybridizing region that is at least 80%, at least 85%, at least 90%, at least 95%, or 100% complementary to a target nucleic acid sequence corresponding to positions 37-74 of SEQ ID NO: 23 or a complement thereof. In some embodiments, a FIP primer further comprises a second target hybridizing region that hybridizes to at least 15 contiguous nucleotides present in a target nucleic acid sequence corresponding to positions 117-152 of SEQ ID NO: 23 or a complement thereof. In some embodiments, a FIP primer further comprises a second target hybridizing region that is at least 80%, at least 85%, at least 90%, at least 95%, or 100% complementary to a target nucleic acid sequence corresponding to positions 117-152 of SEQ ID NO: 23 or a complement thereof. In some embodiments, a FIP primer comprises at least one target nucleic acid hybridization region sequence having at least 80%, at least 85%, at least 90%, at least 95%, or 100% identify to a target nucleic acid hybridization region sequence of any of SEQ ID NOs: 10-18. In some embodiments, a FIP primer comprises at least one target nucleic acid hybridization region sequence differing by no more than 1, 2, or 3 nucleotides from a target nucleic acid hybridization region sequence of any of SEQ ID NOs: 10-18. In some embodiments, a FIP primer comprises a nucleic acid sequence having at least 80%, at least 85%, at least 90%, at least 95%, or 100% identify to the nucleic acid sequence of any of SEQ ID NOs: 10-18. In some embodiments, a FIP primer comprises a nucleic acid sequence differing by no more than 1, 2, 3, 4, or 5 nucleotides from the nucleic acid sequence of any of SEQ ID NOs: 10-18. In some embodiments, a FIP primer comprises the nucleic acid sequence of any of SEQ ID NOs: 10-18. In some embodiments, a FIP primer consists of any of SEQ ID NOs: 10-18. The FIP primer is able to hybridize to a target nucleic acid or amplicon thereof and initiate nucleic acid polymerization. In some embodiments, the FIP primer first target hybridizing region hybridizes to a region of a complement of SEQ ID NO: 23 and the FIP primer second target hybridizing region hybridizes to a region of SEQ ID NO: 23.

In some embodiments, a FL primer comprises a target hybridizing region that hybridizes to at least 15 contiguous nucleotides present in a target nucleic acid sequence corresponding to positions 76-112 of SEQ ID NO: 23 or a complement thereof. In some embodiments, a FL primer comprises a target hybridizing region that is at least 80%, at least 85%, at least 90%, at least 95%, or 100% complementary to a target nucleic acid sequence corresponding to positions 76-112 of SEQ ID NO: 23 or a complement thereof. In some embodiments, a FL primer comprises a nucleic acid sequence having at least 80%, at least 85%, at least 90%, at least 95%, or 100% identify to the nucleic acid sequence of SEQ ID NO: 19. In some embodiments, a FL primer comprises a nucleic acid sequence differing by no more than 1, 2, or 3 nucleotides from the nucleic acid sequence of SEQ ID NO: 19. In some embodiments, a FL primer comprises the nucleic acid sequence of SEQ ID NO: 19. In some embodiments, a FL primer consists of SEQ ID NO: 19. The FL primer is able to hybridize to a target nucleic acid or amplicon thereof and initiate nucleic acid polymerization. In some embodiments, the F3 primer hybridizes to a region of SEQ ID NO: 23.

In some embodiments, a B3 primer comprises a target hybridizing region that hybridizes to at least 15 contiguous nucleotides present in a target nucleic acid sequence corresponding to positions 335-366 of SEQ ID NO: 23 or a complement thereof. In some embodiments, a B3 primer comprises a target hybridizing region that is at least 80%, at least 85%, at least 90%, at least 95%, or 100% complementary to a target nucleic acid sequence corresponding to positions 335-366 of SEQ ID NO: 23 or a complement thereof. In some embodiments, a B3 primer comprises a nucleic acid sequence having at least 80%, at least 85%, at least 90%, at least 95%, or 100% identify to the nucleic acid sequence of SEQ ID NO: 20. In some embodiments, a B3 primer comprises a nucleic acid sequence differing by no more than 1, 2, or 3 nucleotides from the nucleic acid sequence of SEQ ID NO: 20. In some embodiments, a B3 primer comprises the nucleic acid sequence of SEQ ID NO: 20. In some embodiments, a B3 primer consists of SEQ ID NO: 20. The B3 primer is able to hybridize to a target nucleic acid or amplicon thereof and initiate nucleic acid polymerization. In some embodiments, the B3 primer hybridizes to a region of SEQ ID NO: 23.

In some embodiments, a BIP primer comprises a target hybridizing region that hybridizes to at least 15 contiguous nucleotides present in a target nucleic acid sequence corresponding to positions 247-279 of SEQ ID NO: 23 or a complement thereof. In some embodiments, a BIP primer comprises a first target hybridizing region that is at least 80%, at least 85%, at least 90%, at least 95%, or 100% complementary to a target nucleic acid sequence corresponding to positions 247-279 of SEQ ID NO: 23 or a complement thereof. In some embodiments, a BIP primer further comprises a second target hybridizing region that hybridizes to at least 15 contiguous nucleotides present in a target nucleic acid sequence corresponding to positions 154-188 of SEQ ID NO: 23 or a complement thereof. In some embodiments, a BIP primer further comprises a second target hybridizing region that is at least 80%, at least 85%, at least 90%, at least 95%, or 100% complementary to a target nucleic acid sequence corresponding to positions 154-188 of SEQ ID NO: 23 or a complement thereof. In some embodiments, a BIP primer comprises at least one target nucleic acid hybridization region sequence differing by no more than 1, 2, or 3 nucleotides from a target nucleic acid hybridization region sequence of SEQ ID NO: 21. In some embodiments, a BIP primer comprises a nucleic acid sequence having at least 80%, at least 85%, at least 90%, at least 95%, or 100% identify to the nucleic acid sequence of SEQ ID NO: 21. In some embodiments, a BIP primer comprises a nucleic acid sequence differing by no more than 1, 2, 3, 4, or 5 nucleotides from the nucleic acid sequence of SEQ ID NO: 21. In some embodiments, a BIP primer comprises the nucleic acid sequence of SEQ ID NO: 21. In some embodiments, a BIP primer consists of SEQ ID NO: 21. The BIP primer is able to hybridize to a target nucleic acid or amplicon thereof and initiate nucleic acid polymerization. In some embodiments, the BIP primer first target hybridizing region hybridizes to a region of SEQ ID NO: 23 and the BIP primer second target hybridizing region hybridizes to a region of a complement of SEQ ID NO: 23.

In some embodiments, a BL primer comprises a target hybridizing region that hybridizes to at least 15 contiguous nucleotides present in a target nucleic acid sequence corresponding to positions 217-242 of SEQ ID NO: 23 or a complement thereof. In some embodiments, a BL primer comprises a target hybridizing region that is at least 80%, at least 85%, at least 90%, at least 95%, or 100% complementary to a target nucleic acid sequence corresponding to positions 217-242 of SEQ ID NO: 23 or a complement thereof. In some embodiments, a BL primer comprises a nucleic acid sequence having at least 80%, at least 85%, at least 90%, at least 95%, or 100% identify to the nucleic acid sequence of SEQ ID NO: 22. In some embodiments, a BL primer comprises a nucleic acid sequence differing by no more than 1, 2, or 3 nucleotides from the nucleic acid sequence of SEQ ID NO: 22. In some embodiments, a BL primer comprises the nucleic acid sequence of SEQ ID NO: 22. In some embodiments, a BL primer consists of SEQ ID NO: 22. The BL primer is able to hybridize to a target nucleic acid or amplicon thereof and initiate nucleic acid polymerization. In some embodiments, the BL primer hybridizes to a region of a complement of SEQ ID NO: 23.

Any of the described primers can contain one or more modified nucleotides. In some embodiments, any of the described primers can contain two or more modified nucleotides. The two or more modified nucleotides may have the same or different modifications.

Any of the described LAMP primers can comprise one or more degenerate positions. A "degenerate" position in an oligonucleotide refers to a position where more than one base is present in a population of oligonucleotides. Oligomers with degenerate positions can be synthesized by providing a mixture of nucleotide precursors corresponding to the desired degenerate combination at the step of the synthesis where incorporation of a degenerate position is desired. Oligonucleotides may be synthesized as degenerate. Alternatively, oligonucleotides may be synthesized as individual species and then subsequently mixed. A degenerate position can be N (A, C, G, or T), R (A or G), Y (C or T), S (G or C), W (A or T), K (G or T), M (A or C), B (C, G, or T), D (A, G, or T), H (A, C, or T), or V (A, C, or G). In some embodiments, a LAMP primer contains 1, 2, 3, 4, and 5 degenerate positions. In some embodiments, a LAMP primer contains 1 degenerate position. In some embodiments, a LAMP primer contains 2 degenerate positions. In some embodiments, a LAMP primer contains 3 degenerate positions. In some embodiments, a LAMP primer contains 4 degenerate positions. In some embodiments, a LAMP primer contains 5 degenerate positions. In some embodiments, the F3 primer contains 0, 1, or 3 degenerate positions. In some embodiments, the F3 primer contains 2 degenerate positions. In some embodiments, the F3 primer contains a degenerate nucleotide at a position corresponding to position 9 of SEQ ID NO: 23. The degenerate nucleotide at a position corresponding to position 9 of SEQ ID NO: 23 can be S (G or C). In some embodiments, the F3 primer contains a degenerate nucleotide at a position corresponding to position 15 of SEQ ID NO: 23. The degenerate nucleotide at a position corresponding to position 15 of SEQ ID NO: 23 can be W (A or T). In some embodiments, the F3 primer contains degenerate nucleotides at positions corresponding to positions 9 and 15 of SEQ ID NO: 23. The degenerate nucleotide at positions corresponding to positions 9 and 15 of SEQ ID NO: 23 can be S and W respectively. In some embodiments, the FIP primer contains 0, 1, or 3 degenerate positions. In some embodiments, the FIP primer contains 2 degenerate positions. In some embodiments, the FIP primer contains a degenerate nucleotide at positions corresponding to positions 44 and/or 59 of SEQ ID NO: 23. The degenerate nucleotides at positions corresponding to positions 44 and/or 59 of SEQ ID NO: 23 can be W.

In some embodiments, a primer can have a wobble base or a nucleotide that can base pair with two or more of A, C, G, and T.

In some embodiments, the outer primers (F3 and B3) are independently about 15 to about 40 nucleotides in length. In some embodiments, the outer primers (F3 and B3) are independently about 20 to about 30 nucleotides in length. In some embodiments, the outer primers (F3 and B3) are independently about 25 to about 30 nucleotides in length. In some embodiments, the outer primers (F3 and B3) are independently 25, 26, 27, 28, 29, or 30 nucleotides in length.

In some embodiments, the inner primers (FIP and BIP) are independently about 30 to about 80 nucleotides in length. In some embodiments, the inner primers (FIP and BIP) are independently about 65 to about 75 nucleotides in length. In some embodiments, the inner primers (FIP and BIP) are independently 65, 66, 67, 68, 69, 70, 71, 72, 73, 74, or 75 nucleotides in length.

In some embodiments, the loop primers (FL and BL) are independently about 15 to about 40 nucleotides in length. In some embodiments, the loop primers (FL and BL) are independently about 30 to about 40 nucleotides in length. In some embodiments, the loop primers (FL and BL) are independently 30, 31, 22, 33, 34, 35, 36, 37, 38, 39, or 40 nucleotides in length.

III. Kits

Described are compositions and kits for amplifying, detecting and/or quantifying SARS-CoV-related betacoronavirus. The described compositions and kits can provide for the direct, rapid, and sensitive detection of SARS-CoV-related betacoronavirus. In some embodiments, the described compositions and kits provide POCTs for SARS-CoV-related betacoronavirus.

Any of the described oligonucleotides, primer sets, or compositions comprising the described oligonucleotides or primer sets may be packaged or included in a kit, container, pack, or dispenser. In some embodiments, any primer combination described herein is provided in a kit. Any of the described oligonucleotides, primer sets, or compositions comprising the described oligonucleotides or primer sets may be packaged in pre-filled syringes or vials. The oligonucleotides, primer sets, or compositions comprising the described oligonucleotides or primer sets may be provided as one or more lyophilized powder(s), in one or more solutions, or combinations thereof.

In some embodiments, kit contains at least one container containing a described coronavirus LAMP assay primer set. In some embodiments, a kit contains two or more containers each containing a described coronavirus LAMP assay primer set. In some embodiments, a kit contains a multi-well plate wherein at least one well contains a described coronavirus LAMP assay primer set. In some embodiments, the primer set comprises a F3 primer, a FIB primer, a B3 primer, and a BIP primer. In some embodiments, the primer set comprises a F3 primer, a FIB primer, a FL primer, a B3 primer, a BIP primer and a BF primer.

In some embodiments, a kit further comprises a reaction mixture. The reaction mixture can be provided in a separate container or the primers can be provided in a container that further contains the reaction mixture. In some embodiments, one or more components of a reaction mixture can be provided in a single or separate containers. A reaction mixture may comprise one or more reagents suitable for performing isothermal loop-mediated amplification. The reaction mixture can comprise one or more of: dNTPs, buffer, colorimetric agent, pH-sensitive dye that changes color upon acidification, metal ion indicator, DNA polymerase, uracil DNA glycosylase, guanidine hydrochloride, helicase, a detection probe, virus inactivation agent, and RNA release agent.

In some embodiments, the reaction mixture comprises dNTPs. The dNTPs can comprise dATP, dCTP, dGTP, and dTTP or dATP, dCTP, dGTP, dTTP, and dUTP. In some embodiments, the dNTPs comprise dATP, dCTP, dGTP, dTTP, and dUTP, In some embodiments, the dNTPs consist of dATP, dCTP, dGTP, dTTP, and dUTP.

In some embodiments, the reaction mixture comprises a metal ion indicator. The metal ion indicator can be, but is not limited to, calcein, hydroxynaphthol blue, and malachite green. In some embodiments, the metal ion being detected is provided as a salt within the reaction mixture. The metal ion can be, but is not limited to, $Mg^{2+}$ or $Mn^{2+}$.

In some embodiments, the reaction mixture comprises a weakly buffered solution and a pH-sensitive dye that changes color upon acidification. The buffered solution can be, but is not limited to, 10 mM $(NH_4)_2SO_4$, 50 mM KCl, 8 mM $MgSO_4$, 400 µM Tris, and 0.1% v/v Tween-20. Nucleotides (dNTPs), polymerase and reverse transcriptase may also be provided in the buffer. In some embodiments, the buffer further comprises 1.4 mM dNTPs, 0.32 U/µL Bst 2.0 DNA polymerase, and 0.3 U/µL reverse transcriptase. The pH-sensitive dye can be, but is not limited to, phenol red, cresol red, neutral red, or m-cresol purple. In some embodiments, the pH-sensitive dye is phenol red or Cresol red. For kits containing the indicator phenol red or Cresol red, a positive detection of the SARS-CoV-2 RNA sequence may be indicated by a yellow color (amplification occurred, pH-dependent color change from pink to yellow), while a negative result may be indicated by a pink color (no amplification occurred, no color change).

Additional colorimetric agents include, but are not limited to, Eva green and SYBR green.

In some embodiments, reaction mixture comprises a DNA polymerase. In some embodiments, the DNA polymerase comprises a thermostable reverse transcriptase. In some embodiments, the polymerase comprises a strand displacing polymerase. In some embodiments, the polymerase comprises a thermostable strand displacing reverse transcriptase. The polymerase can be, but is not limited to, *Bacillus stearothermophilus* (Bst) DNA polymerase. The Bst DNA polymerase can be a modified Bst DNA polymerase designed to have increased reverse transcriptase activity compared to unmodified Bst DNA polymerase.

In some embodiments, the DNA polymers comprises a warm-start activated polymerase. A warm start activated polymerase can be reversibly inhibited by reversible, aptamer-based inhibition. A warm-start polymerase can be, but is not limited to, a Bst WarmStart DNA Polymerase.

In some embodiments, the reaction mixture further comprises a uracil DNA glycosylase (UDG). The UDG can be, but is not limited to, an Antarctic thermolabile uracil DNA glycosylase.

In some embodiments, the kit may contain a sample prep or lysis buffer containing guanidine hydrochloride.

In some embodiments, the reaction mixture further comprises a helicase. The helicase can be, but is not limited to, a *Thermoanaerobacter tengcongensis* (Tte) UvrD Helicase.

In some embodiments, the reaction mixture further comprises a detection oligonucleotide (probe).

A kit may further comprise one or more controls selected from the groups consisting of: positive control test sample containing a betacoronavirus target nucleic acid sequence, a negative control test sample that does not contain a betacoronavirus target nucleic acid, and a housekeeping gene control sample that contains a primer set designed to amplify a housekeeping gene nucleic acid sequence. The positive control betacoronavirus target nucleic acid can be a plasmid containing the betacoronavirus target nucleic acid sequence. The housekeeping gene can be, but is not limited, to an actin gene target sequence.

In some embodiments, a kit further comprises at least one swab. The swab is selected as appropriate for the type of sample to be taken from a subject. The swab can be, but is not limited to, a flocked swab, a flocked tapered swab, a spun polyester swab, a Dacron (polyethylene terephthalate polyester) swab, or a rayon swab.

In some embodiments, a kit further comprises transport media, viral transport media, Amies transport media, or sterile saline.

A kit may further contain one or more of: instructions for use or a notice in a form prescribed by a governmental agency regulating the manufacture, use or sale of the products. The instructions may be associated with a package insert and/or the packaging of the kit or the components thereof.

IV. SARS-CoV-Related Betacoronavirus Amplification/Detection

Described are methods of amplifying, detecting and/or quantifying SARS-CoV-related betacoronavirus nucleic acid using one or more of the described LAMP primer sets, compositions, or kits. In some embodiments, amplification comprises contacting a sample with one or more of the described LAMP primer sets or compositions and performing an in vitro nucleic acid amplification reaction, wherein SARS-CoV-related betacoronavirus target nucleic acid, if present in the sample, is used as template for generating an amplification product (amplicon). In some embodiments, the methods further comprise detecting the presence or absence of the amplification product, thereby indicating the presence or absence of SARS-CoV-related betacoronavirus in the sample. Various methods in the art can be used to detect the amplified SARS-CoV-related betacoronavirus nucleic acid amplicon. A detection step may be performed using any of a variety of known techniques to detect a LAMP amplicon. Methods of detecting the coronavirus LAMP amplification product include, but are not limited to, colorimetric assay, photometry, fluorescence of loop primer upon self-dequenching-LAMP (FLOS-LAMP), electrophoresis analysis, turbidity analysis, intercalating dye detection, metal ion indicator analysis, and detection oligonucleotides (e.g., molecular beacons). Detection of a SARS-CoV-related betacoronavirus amplification product indicates presence of the SARS-CoV-related betacoronavirus in the sample. In some embodiments, detection of a SARS-CoV-related betacoronavirus amplification product in a sample from a subject indicates the subject is infected with the SARS-CoV-related betacoronavirus.

In some embodiments, the methods further comprise virus inactivation.

In some embodiments, the methods further comprise an RNA release step.

The sample may be a biological sample obtained from a subject. The sample may be purified to remove or reduce one or more components in the sample prior to contacting the sample the with one or more of the described LAMP primer sets or compositions or performing a loop-mediated isothermal amplification reaction on the sample using the described kits.

The described LAMP primer sets can be used to amplify a SARS-CoV-related betacoronavirus sequence. The amplified SARS-CoV-related betacoronavirus sequence, the amplicon, may include all or a portion of a SARS-CoV-related betacoronavirus corresponding to SEQ ID NO: 23 and/or a complement thereof.

In some embodiments, detection of SARS-CoV-related betacoronavirus in a sample can be used to aid in the management, quarantine, isolation, and/or treatment of a subject. In some embodiments, detecting the presence or absence of SARS-CoV-related betacoronavirus in a sample is used to diagnose SARS-CoV-related betacoronavirus infection in a subject.

Any of the primers or primer sets disclosed herein and any combinations (e.g., kits and compositions) comprising such primers or primer sets are to be understood as also disclosed for use in amplifying, detecting and/or quantifying SARS-CoV-related betacoronavirus, and for use in the preparation of a composition for amplifying, detecting and/or quantifying SARS-CoV-related betacoronavirus.

In some embodiments, the amplification and/or detection of a SARS-CoV-related betacoronavirus target nucleic acid using the described compositions or kits does not require specialized equipment other than a simple heat block or similar device.

In some embodiments, the described SARS-CoV-related betacoronaviruses detection kits and methods provide real time visual results via color change. In some embodiments, the described SARS-CoV-related betacoronaviruses detection tests and methods provide real time visual results via color change endpoint in 45 minutes or less.

TABLE 1

| SARS-CoV-related betacoronavirus LAMP primers | | |
|---|---|---|
| Primer | Sequence | SEQ ID NO |
| F3 | GAACATGTSCAAATWCACACAATCGACGG | 1 |
| F3 | GAACATGTSCAAATACACACAATCGACGG | 2 |

TABLE 1-continued

| SARS-CoV-related betacoronavirus LAMP primers | | |
|---|---|---|
| Primer | Sequence | SEQ ID NO |
| F3 | GAACATGTSCAAATTCACACAATCGACGG | 3 |
| F3 | GAACATGTCCAAATWCACACAATCGACGG | 4 |
| F3 | GAACATGTGCAAATWCACACAATCGACGG | 5 |
| F3 | GAACATGTGCAAATACACACAATCGACGG | 6 |
| F3 | GAACATGTGCAAATTCACACAATCGACGG | 7 |
| F3 | GAACATGTCCAAATTCACACAATCGACGG | 8 |
| F3 | GAACATGTCCAAATACACACAATCGACGG | 9 |
| FIP | TCTTCCGAAACGAATGAGTACATAAGTTCGTACTCAGGAGTTGWTAATCCAG TAATGGWACCAATTTATGATGA | 10 |
| FIP | TCTTCCGAAACGAATGAGTACATAAGTTCGTACTCAGGAGTTGWTAATCCAG TAATGGAACCAATTTATGATGA | 11 |
| FIP | TCTTCCGAAACGAATGAGTACATAAGTTCGTACTCAGGAGTTGWTAATCCAG TAATGGTACCAATTTATGATGA | 12 |
| FIP | TCTTCCGAAACGAATGAGTACATAAGTTCGTACTCAGGAGTTGATAATCCAG TAATGGWACCAATTTATGATGA | 13 |
| FIP | TCTTCCGAAACGAATGAGTACATAAGTTCGTACTCAGGAGTTGTTAATCCAG TAATGGWACCAATTTATGATGA | 14 |
| FIP | TCTTCCGAAACGAATGAGTACATAAGTTCGTACTCAGGAGTTGATAATCCAG TAATGGAACCAATTTATGATGA | 15 |
| FIP | TCTTCCGAAACGAATGAGTACATAAGTTCGTACTCAGGAGTTGATAATCCAG TAATGGTACCAATTTATGATGA | 16 |
| FIP | TCTTCCGAAACGAATGAGTACATAAGTTCGTACTCAGGAGTTGTTAATCCAG TAATGGTACCAATTTATGATGA | 17 |
| FIP | TCTTCCGAAACGAATGAGTACATAAGTTCGTACTCAGGAGTTGTTAATCCAG TAATGGTACCAATTTATGATGA | 18 |
| FL | CTTGTGCTTACAAAGGCACGCTAGTAGTCGTCGTCGG | 19 |
| B3 | TTAGTTCGTTTAGACCAGAAGATCAGGAACTC | 20 |
| BIP | ACAGCTACGTTAATAGTTAATAGCGTACTTCTTTTACTCACGTTACCAATAT TGCAGCAGTACGCACA | 21 |
| BL | ACACTAGCCATCCTTACTGCGCTTCG | 22 |

TABLE 2

| Exemplary Primer sets | | | |
|---|---|---|---|
| | Primer set | | |
| primer | SEQ ID NO: | SEQ ID NO: | SEQ ID NO: |
| F3 | any one or more of 1-9 | 1 | 6-9 |
| FIP | any one or more of 10-19 | 10 | 15-18 |
| FL | 19 | 19 | 19 |
| B3 | 20 | 20 | 20 |
| BIP | 21 | 21 | 21 |
| BL | 22 | 22 | 22 |

LISTING OF EMBODIMENTS

1. A LAMP primer set for amplification of a SARS-CoV-related betacoronavirus target nucleic acid, comprising: a forward outer (F3) primer, a forward inner (BIP) primer, a backward outer (B3) primer, and a backward inner (BIP) primer configured to amplify a SARS-CoV-related betacoronavirus target nucleic acid corresponding to SEQ ID NO: 3 or a fragment thereof by loop-mediated isothermal amplification.

2. The LAMP primer set of embodiment 1, wherein:

(a) the F3 primer comprises a target hybridizing region that hybridizes to at least 15 contiguous nucleotides present in a target nucleic acid sequence corresponding to positions 1-29 of SEQ ID NO: 23 or a complement thereof;

(b) the FIP primer comprises a first target hybridizing region that hybridizes to at least 15 contiguous nucleotides present in a target nucleic acid sequence corresponding to positions 37-74 of SEQ ID NO: 23 or a complement thereof and a second target hybridizing region that hybridizes to at least 15 contiguous nucleotides present in a target nucleic acid sequence corresponding to positions 117-152 of SEQ ID NO: 23 or a complement thereof;

(c) the B3 primer comprises a target hybridizing region that hybridizes to at least 15 contiguous nucleotides present in a target nucleic acid sequence corresponding to positions 335-366 of SEQ ID NO: 23 or a complement thereof; and (d) the BIP primer comprises a first target hybridizing region that hybridizes to at least 15 contiguous nucleotides present in a target nucleic acid sequence corresponding to positions 247-279 of SEQ ID NO: 23 or a complement thereof and second target hybridizing region that hybridizes to at least 15 contiguous nucleotides present in a target nucleic acid sequence corresponding to positions 154-188 of SEQ ID NO: 23 or a complement thereof.

3. The LAMP primer set of embodiment 1, wherein:

(a) the F3 primer comprises a target hybridizing region that is at least 80%, at least 85%, at least 90%, at least 95%, or 100% complementary to a target nucleic acid sequence corresponding to positions 1-29 of SEQ ID NO: 23 or a complement thereof;

(b) the FIP primer comprises a target hybridizing region that is at least 80%, at least 85%, at least 90%, at least 95%, or 100% complementary to a target nucleic acid sequence corresponding to positions 37-74 of SEQ ID NO: 23 or a complement thereof and a second target hybridizing region that is at least 80%, at least 85%, at least 90%, at least 95%, or 100% complementary to a target nucleic acid sequence corresponding to positions 117-152 of SEQ ID NO: 23 or a complement thereof;

(c) the B3 primer comprises a target hybridizing region that is at least 80%, at least 85%, at least 90%, at least 95%, or 100% complementary to a target nucleic acid sequence corresponding to positions 335-366 of SEQ ID NO: 23 or a complement thereof; and (d) the BIP primer comprises a first target hybridizing region that is at least 80%, at least 85%, at least 90%, at least 95%, or 100% complementary to a target nucleic acid sequence corresponding to positions 247-279 of SEQ ID NO: 23 or a complement thereof and a second target hybridizing region that is at least 80%, at least 85%, at least 90%, at least 95%, or 100% complementary to a target nucleic acid sequence corresponding to positions 154-188 of SEQ ID NO: 23 or a complement thereof.

4. The LAMP primer set of embodiment 1, wherein:

(a) the F3 primer comprises a nucleic acid sequence having at least 80%, at least 85%, at least 90%, at least 95%, or 100% identify to the nucleic acid sequence of any of SEQ ID NOs: 1-9;

(b) the FIP primer comprises a nucleic acid sequence having at least 80%, at least 85%, at least 90%, at least 95%, or 100% identify to the nucleic acid sequence of any of SEQ ID NOs: 10-18;

(c) the B3 primer comprises a nucleic acid sequence having at least 80%, at least 85%, at least 90%, at least 95%, or 100% identify to the nucleic acid sequence of SEQ ID NO: 20; and (d) the BIP primer comprises a nucleic acid sequence having at least 80%, at least 85%, at least 90%, at least 95%, or 100% identify to the nucleic acid sequence of SEQ ID NO: 21.

5. The LAMP primer set of embodiment 1, wherein:

(a) the F3 primer comprises a nucleic acid sequence differing by no more than 1, 2, or 3 nucleotides from the nucleic acid sequence of any of SEQ ID NOs: 1-9;

(b) the FIP primer comprises a nucleic acid sequence differing by no more than 1, 2, 3, 4, or 5 nucleotides from the nucleic acid sequence of any of SEQ ID NOs: 10-18;

(c) the B3 primer comprises nucleic acid sequence differing by no more than 1, 2, or 3 nucleotides from the nucleic acid sequence of SEQ ID NOs: 20; and (d) the BIP primer comprises a nucleic acid sequence differing by no more than 1, 2, 3, 4, or 5 nucleotides from the nucleic acid sequence of SEQ ID NO: 21.

6. The LAMP primer set of embodiment 1, wherein:

(a) the F3 primer comprises the nucleic acid sequence of any of SEQ ID NOs: 1-9;

(b) the FIP primer comprises the nucleic acid sequence of any of SEQ ID NOs: 10-18;

(c) the B3 primer comprises the nucleic acid sequence of SEQ ID NO: 20; and (d) the BIP primer comprises the nucleic acid sequence of SEQ ID NO: 21.

7. The LAMP primer set of embodiment 1, wherein:

(a) the F3 primer consists of any of SEQ ID NOs: 1-9;

(b) the FIP primer consists of any of SEQ ID NOs: 10-18;

(c) the B3 primer consists of SEQ ID NO: 20; and (d) the BIP primer consists of SEQ ID NO: 21.

8. The LAMP primer set of embodiment 1, wherein:

(a) the F3 primer comprises SEQ ID NO: 1;

(b) the FIP primer comprises SEQ ID NO: 10;

(c) the B3 primer comprises SEQ ID NO: 20; and (d) the BIP primer comprises SEQ ID NO: 21.

9. The LAMP primer set of any one of embodiments 1-8, further comprising a forward loop (FL) primer and a backward loop (BL) primer.

10. The LAMP primer set of embodiment 9, wherein:

(a) the FL primer comprises a target hybridizing region that hybridizes to at least 15 contiguous nucleotides present in a target nucleic acid sequence corresponding to positions 76-112 of SEQ ID NO: 23 or a complement thereof; and (b) the BL primer comprises a target hybridizing region that hybridizes to at least 15 contiguous nucleotides present in a target nucleic acid sequence corresponding to positions 217-242 of SEQ ID NO: 23 or a complement thereof.

11. The LAMP primer set of embodiment 9, wherein:

(a) the FL primer comprises a target hybridizing region that is at least 80%, at least 85%, at least 90%, at least 95%, or 100% complementary to a target nucleic acid sequence corresponding to positions 76-112 of SEQ ID NO: 23 or a complement thereof; and (b) the BL primer comprises a target hybridizing region that is at least 80%, at least 85%, at least 90%, at least 95%, or 100% complementary to a target nucleic acid sequence corresponding to positions 217-242 of SEQ ID NO: 23 or a complement thereof.

12. The LAMP primer set of embodiment 9, wherein:

(a) the FL primer comprises a nucleic acid sequence having at least 80%, at least 85%, at least 90%, at least 95%, or 100% identify to the nucleic acid sequence of SEQ ID NO: 19; and (b) the BL primer comprises a nucleic acid sequence having at least 80%, at least 85%, at least 90%, at least 95%, or 100% identify to the nucleic acid sequence of SEQ ID NO: 22.

13. The LAMP primer set of embodiment 9, wherein:

(a) the FL primer comprises a nucleic acid sequence differing by no more than 1, 2, or 3 nucleotides from the nucleic acid sequence of SEQ ID NOs: 19; and

(b) the BL primer comprises a nucleic acid sequence differing by no more than 1, 2, or 3 nucleotides from the nucleic acid sequence of SEQ ID NO: 22.

14. The LAMP primer set of embodiment 9, wherein:
(a) the FL primer comprises the nucleic acid sequence of SEQ ID NO: 19; and
(b) the BL primer comprises the nucleic acid sequence of SEQ ID NO: 22.

15. The LAMP primer set of embodiment 9, wherein:
(a) the FL primer consists of SEQ ID NO: 19; and
(b) the BL primer consists of SEQ ID NO: 22.

16. The LAMP primer set of any one of embodiments 1-3 or 9-11, wherein one or more of the primers contains one or more degenerate positions.

17. The LAMP primer set of any one of embodiments 1-16, wherein one or more of the primers contains one or more modified nucleotides, one or more wobble bases, or one or more nucleotides that can base pair with two or more of A, C, G, and T.

18. A kit for amplifying or detecting a SARS-CoV-related betacoronavirus, wherein the kit comprises the LAMP primer set of any one of embodiments 1-17.

19. The kit of embodiment 18, wherein the kit further comprises a reaction mixture.

20. The kit of embodiment 19, wherein the reaction mixture comprises one or more of: dNTPs, buffer, colorimetric agent, pH-sensitive dye that changes color upon acidification, metal ion indicator, DNA polymerase, uracil DNA glycosylase, guanidine hydrochloride, helicase, a detection probe, virus inactivation agent, and RNA release agent.

21. The kit of embodiment 20, wherein the colorimetric agent comprises calcein, hydroxynaphthol blue, malachite green, phenol red, cresol red, neutral red, m-cresol purple, Eva green, or SYBR green.

22. The kit of embodiment 20 or 21, wherein the DNA polymerase comprises a thermostable strand displacing reverse transcriptase.

23. The kit of embodiment 22, wherein the thermostable strand displacing reverse transcriptase comprises a *Bacillus stearothermophilus* (Bst) DNA polymerase, a modified Bst DNA polymerase, or a Bst WarmStart DNA Polymerase.

24. The kit of any one of embodiments 20-23, wherein the uracil DNA glycosylase comprises an Antarctic thermolabile uracil DNA glycosylase.

25. The kit of any one of embodiments 20-24, wherein the kit comprises 40±20 mM, 40±15 mM, 40±10 mM, or 40±5 mM guanidine hydrochloride.

26. The kit of any one of embodiments 19-25, wherein the kit further comprises one or more of: (a) a positive control test sample containing a betacoronavirus target nucleic acid sequence; (b) a negative control test sample that does not contain a betacoronavirus target nucleic acid; and (c) a housekeeping gene control sample that contains a primer set designed to amplify a housekeeping gene nucleic acid sequence.

27. The kit of any one of embodiments 19-26, wherein the kit further comprises instructions for use or a notice in a form prescribed by a governmental agency regulating the manufacture, use or sale of the products.

28. A method of amplifying or detecting a SARS-CoV-related betacoronavirus in a sample, comprising performing a loop-mediated isothermal amplification reaction on the sample using the kit of any one of embodiments 18-27, wherein the SARS-CoV-related betacoronavirus target nucleic acid, if present in the sample, is used as template for generating an amplification product, and optionally detecting the presence or absence of the amplification product.

29. The method of embodiment 28, wherein detecting the presence or absence of the amplification product comprises observing a color or turbidity change.

30. The method of embodiment 29, wherein the sample is a clinical sample obtained from a subject.

31. The method of embodiment 30, wherein the sample comprises a saliva sample or RNA extracted from saliva.

32. A method of diagnosing SARS-CoV-related betacoronavirus infection in a subject, comprising: performing a loop-mediated isothermal amplification reaction on the sample using the kit of any one of embodiments 18-27; performing a loop-mediated isothermal amplification reaction, wherein the SARS-CoV-related betacoronavirus target nucleic acid, if present in the sample, is used as template for generating an amplification product; and detecting the presence or absence of the amplification product, wherein detecting the presence of the amplification product indicates SARS-CoV-related betacoronavirus infection.

33. The method of embodiment 32, wherein the sample is a clinical sample obtained from a subject.

34. The method of embodiment 33, wherein the sample comprises a saliva sample or RNA extracted from saliva.

35. The LAMP primer set of any one of embodiments 1-17, the kit of any one of embodiments 18-27, or the method of any one of embodiments 28-30, wherein the SARS-CoV-related betacoronavirus is SARS-CoV, SARS-CoV-2, or a variant thereof.

EXAMPLES

Example 1. SARS-CoV-Related Betacoronaviruses Target Nucleic Acid

Alignment of 2003 SARS-CoV, 2019 SARS-CoV-2, and bat origin betacoronavirus genomes was generated in MUSCLE and used to design LAMP primer sets each consisting of 6 primers targeting 8 conserved binding sites. The core LAMP primer sets each correspond to traditional forward and backward outer primers (F3 and B3), forward and backward inner primers (FIP and BIP), and loop-specific primers (FL and BL) Minimal degeneracy was permitted to allow for recognition of multiple bat and SAR-CoV-related betacoronaviruses.

Example 2. LAMP Detection of Coronavirus

Figure 2:
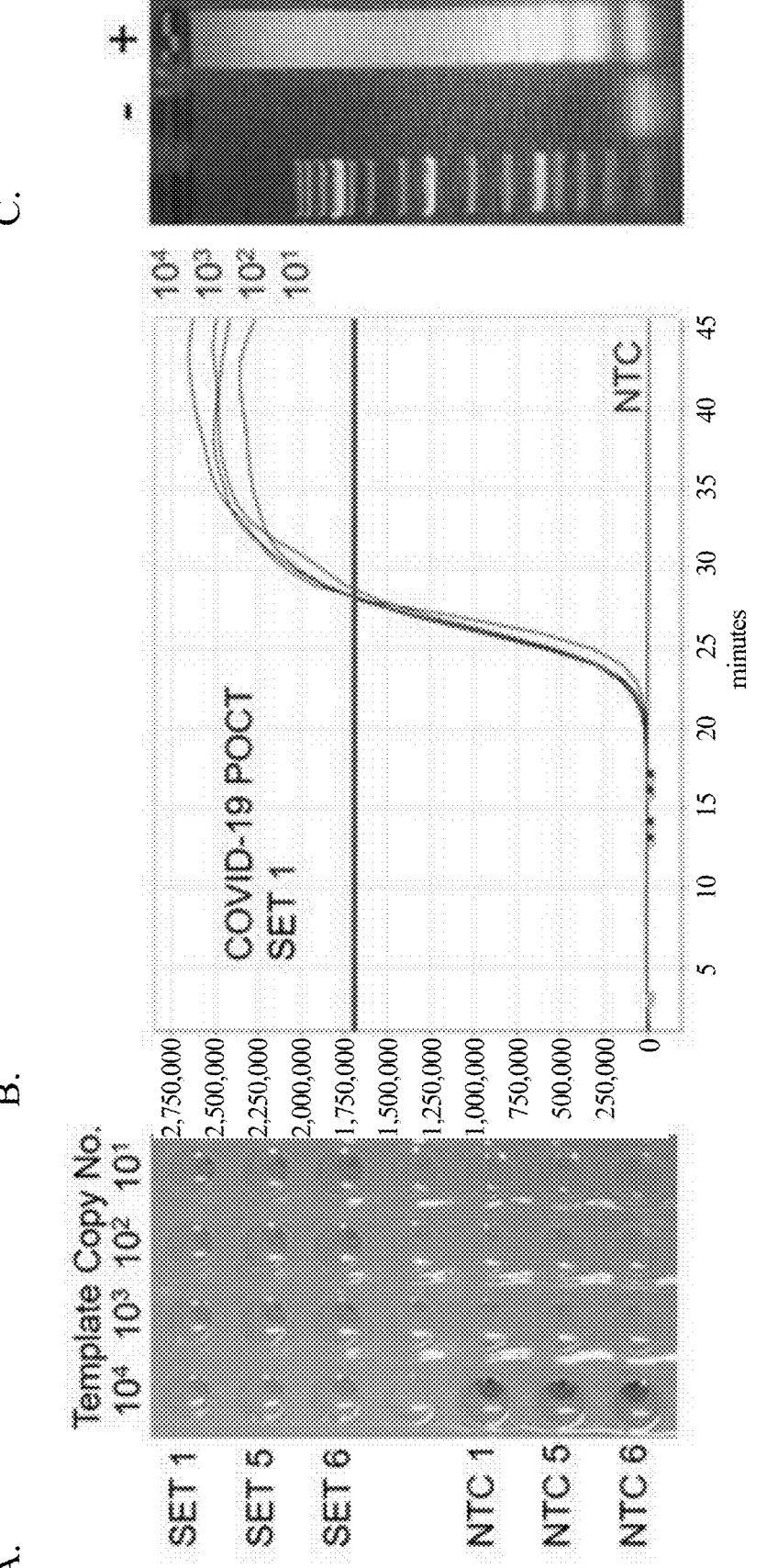
FIG. 2. COVID-19 POCT. Serial 10 fold dilutions of SARS-CoV-2 cDNA were detected by LAMP using three primer sets (SET 1, SET 5, and SET 6) each consisting of 6 primers targeting 8 conserved regions shared among SARS-CoV-related betacoronaviruses genomes. A. Image illustrating visual positive results (test samples for SET1, SET5, and SET6 were yellow (positive) for each concentration of targeting nucleic acid tested) achieved in less than 30 min; no template controls (NTC) remained negative (all three negative control samples were negative pink (negative)). B. Graph illustrating fluorescence incorporation in a QuantStudio 3 Real-time PCR System using primer SET 1. C. Concatemeric product from SET 1 shown by gel electrophoresis.
Figure 3:
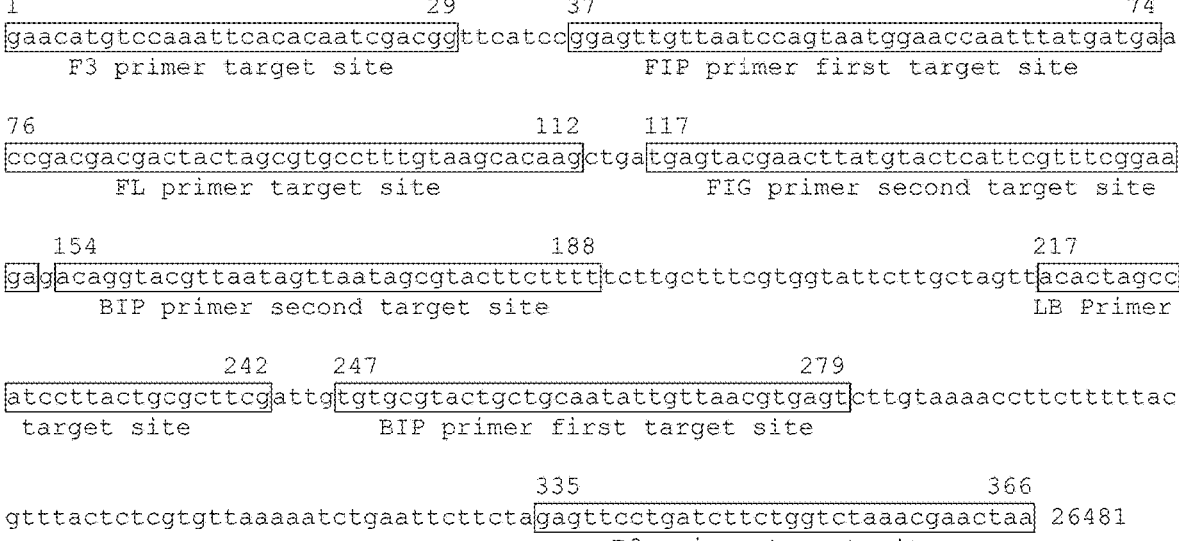
FIG. 3. SARS-CoV-2 target sequence (SEQ ID NO: 23). LAMP primer target nucleic acid sequences are boxed. LAMP primers may target the shown sequence or a complement thereof.

Primer sets identified in example 1 were used to amplify synthetic cDNA and RNA target nucleic acid constructed from SARS-CoV-2 RNA obtained from a University of Florida isolate of SARS-CoV-2. The results are summarized in FIG. 2. The results demonstrate the amplification and detection of SARS-CoV-2 using three different primer sets targeting different conserved regions of the SARS-CoV-2 genome.

Highly reproducible amplification and detection of SARS-CoV-2 was observed with LAMP primer set 1 over a temperature range of 63-68° C. using RNA or cDNA as template. Amplification and detection of SARS-CoV-2 was also observed with LAMP primer sets 5 and 6. The best sensitivity was observed with primer set 1.

TABLE 3

Primer sets

| primer | SET 1 (SEQ ID NO) | SET 5 Sequence (5' → 3') | SEQ ID NO | SET 6 Sequence (5' → 3') | SEQ ID NO |
|---|---|---|---|---|---|
| F3 | 1 | ATGTCTGGTAAAGGCCAACAA CAAC | 25 | GACCACACAAGGCAGATGGGC TAT | 31 |
| FIP | 10 | TTTCCTTGGGTTTGTTCTGGA CCACGTCTAAGGCCAAACTGT CACTAAGAAATCTGCTGC | 26 | GTTAACTACATCTACTTGTGC TATGTAGTTATAAACGTTTTC GCTTTTCCGTTTACGATA | 32 |
| FL | 19 | GCAGTACGTTTTTGCCGAGGC TT | 27 | CGAGAATTCATTCTGCACAAG AGTAGACTAT | 33 |
| B3 | 20 | TGATCTTTGAAATTTGGATCT TTGTCATCCA | 28 | TTACACATTAGGGCTCTTCCA TATAGGC | 34 |
| BIP | 21 | TAATCAGACAAGGAACTGATT ACAAGTTCCCGAAGGTGTGAC TTCCATGCCAATGCG | 29 | TCACATAGCAATCTTTAATCA GTGTGTAACATTAGGTACACT CGATCGTACTCCGCGTGGCCT CG | 35 |
| BL | 22 | ACATTGGCCGCAAATTGCACA ATT | 30 | GGAGGACTTGAAAGAGCCACC AC | 36 |

Example 4. Virus Inactivation and RNA Release Step

Virus inactivation and RNA release are used to provide for simplified or single tube workflow. RNA release increases availably of viral RNA in a sample to reverse transcription and LAMP. Future studies on this workflow will involve the testing of Porcine epidemic diarrhea virus or alternate safe surrogate of coronavirus (test virus) is used to test formulations incorporating virus inactivation and RNA release reagents and methods. LAMP primers specific for the test virus are used with the test virus during testing.

Example 5. Analytical Validation

Specificity of the POCT is assessed using various strains of SARS-CoV-2, genetic near neighbor and look-a-like virus targets. Specificity is tested using synthetic nucleic acid templates, virus culture isolates, or samples obtained from subjects known to be infected with virus. Sensitivity is assessed on limiting dilution of clinical swab samples obtained from subjects infected with or suspected of being infected with SARS-CoV-related betacoronavirus.

Example 6. Diagnostic Validation

The described assay are tested in parallel with RT-qPCR on a limited set of 20-100 known positive and 100-300 known negative deidentified SARS-CoV-2 clinical swab samples. A proficiency test panel is provided to practitioners to train and demonstrate their ability to perform the test correctly as well as to acquire inter and intra-operator variability data. Diagnostic validation is further completed by deployment of the test to sites of COVID-19/SARS-CoV-2 swab sampling with results tabulated and compared to formal diagnostic results from lab RT-qPCR-based testing. It is anticipated that the described SARS-CoV-related betacoronavirus detection compositions and methods will be as or more sensitive and specific than current lab-based RT-qPCR tests. Statistical analyses is performed to further confirm the time to result parameters of the assay, assay sensitivity, specificity, efficiency, and variability when employed on different sample matrices.

Example 7. Limit of Detection on Clinical Samples

Clinical samples were analyzed using the CDC 2019-Novel Coronavirus (2019-nCoV) Real-Time RT-PCR Diagnostic Panel (Singleplex N1) and CDC SARS-CoV-2/RP control multiplex (Multiplex N1) assays as directed and compared with results using a described LAMP assay. Results are summarized in Table 4. The clinical sample were RNA from known positive samples used to validate the CDC PCR test.

TABLE 4

The limit of detection of coronavirus in clinical samples in comparison to CDC 2019n COVID N1 single and multiplex tests = Ct < 26.

| Sample | Dilution | Singleplex N1 | Multiplex N1 | RP (positive control) | LAMP Result |
|---|---|---|---|---|---|
| 1 | 1:10 | 18.366 | 18.489 | 32.167 | Detected |
| | 1:100 | 21.557 | 21.557 | 27.811 | Detected |
| | 1:1,000 | 24.763 | 24.967 | 27.280 | Detected |
| | 1:10,000 | 27.934 | 28.147 | 27.334 | Detected |
| | 1:100,000 | 31.602 | 31.420 | 27.306 | Not Detected |
| 2 | 1:10 | 21.927 | 21.996 | 26.936 | Detected |
| | 1:100 | 25.050 | 25.037 | 27.099 | Detected |
| | 1:1,000 | 28.721 | 28.786 | 27.464 | Not Detected |
| | 1:10,000 | 32.471 | 32.293 | 27.342 | Not Detected |
| | 1:100,000 | 35.989 | 37.364 | 27.540 | Not Detected |
| 3 | 1:10 | 19.624 | 19.215 | 29.861 | Detected |
| | 1:100 | 22.345 | 22.355 | 27.117 | Detected |
| | 1:1,000 | 25.983 | 26.348 | 27.009 | Detected |
| | 1:10,000 | 29.057 | 29.406 | 27.408 | Detected |
| | 1:100,000 | 32.202 | 31.868 | 27.277 | Not Detected |
| 4 | 1:10 | 25.694 | 25.393 | 27.289 | Detected |
| | 1:100 | 28.867 | 28.915 | 27.518 | Not Detected |
| | 1:1,000 | 32.549 | 32.052 | 27.531 | Not Detected |
| | 1:10,000 | Un-determined | 34.990 | 27.319 | Not Detected |
| | 1:100,000 | Un-determined | Un-determined | 27.475 | Not Detected |

The LAMP assay was also used to detect coronavirus in saliva samples directly, without sample preparation.

Example 8. Detection of SARS-CoV-2 in Clinical Samples

RNA samples were collected by the Pathological Lab of the University of Florida. Clinical samples consisted of RNA extracted from human saliva obtained as de-identified samples from the University of FL Pathology lab. Theses clinical samples were analyzed using the CDC 2019-Novel Coronavirus (2019-nCoV) Real-Time RT-PCR Diagnostic Panel (Singleplex N1) assays as directed and compared with results using a described LAMP assay. Results are summarized in Tables 5-7.

For the LAMP Assay, the reaction reagents, including 12.5 µL of buffer, 1 µL of fluorescent dye, 2.5 µL of either SET1 LAMP primers or RNaseP LAMP primers, 2 µL of each clinical sample, and 7 µL of Nuclease-free water to make a final reaction volume of 25 µL were combined in a tube. The reaction was incubated at 65° C. for 45 mins to check for color change.

TABLE 5

| Clinical Samples Trial VAL1-CDC 10-14. | | | | |
|---|---|---|---|---|
| Sample | 2019nCOVID N1 | RP | RTqPCR Result | LAMP Result |
| 04 | 28.20 | 27.60 | Detected | Not Detected |
| 05 | 22.12 | 30.97 | Detected | Detected |
| 14 | 19.90 | 31.11 | Detected | Detected |
| 29 | 19.93 | 32.77 | Detected | Detected |
| 30 | 19.84 | 31.05 | Detected | Detected |
| 39 | 31.97 | 31.32 | Detected | Not Detected |
| 40 | 27.35 | 29.58 | Detected | Not Detected |
| 47 | 9.66 | 24.17 | Detected | Detected |
| 50 | 17.41 | 30.26 | Detected | Detected |
| 65 | 32.89 | 26.00 | Detected | Not Detected |
| 06 | Undetermined | 30.78 | Not Detected | Not Detected |
| 07 | Undetermined | 34.28 | Not Detected | Not Detected |
| 08 | Undetermined | 32.49 | Not Detected | Not Detected |
| 21 | Undetermined | 32.29 | Not Detected | Not Detected |
| 22 | Undetermined | 32.74 | Not Detected | Not Detected |
| 37 | Undetermined | 32.20 | Not Detected | Not Detected |
| 64 | Undetermined | 28.68 | Not Detected | Not Detected |
| 68 | Undetermined | 29.78 | Not Detected | Not Detected |
| 85 | Undetermined | 30.39 | Not Detected | Not Detected |
| 90 | Undetermined | 21.55 | Not Detected | Not Detected |

TABLE 6

| Clinical Samples Trial VAL1-CDC MAA363 | | | | |
|---|---|---|---|---|
| Sample | 2019nCoV N1 | RP | RTqPCR | LAMP Result |
| 20 | 26.85 | 30.27 | Detected | Detected |
| 23 | 23.66 | 27.95 | Detected | Detected |
| 25 | 15.12 | 24.07 | Detected | Detected |
| 42 | 19.25 | Undetermined | Detected | Detected |
| 59 | 32.52 | 29.21 | Detected | Not Detected |
| 75 | 8.25 | Undetermined | Detected | Detected |
| 95 | 16.38 | Undetermined | Detected | Detected |

TABLE 7

| Clinical Samples Trial VAL1-CDC 10-15 | | | | |
|---|---|---|---|---|
| Sample | 2019nCoV N1 | RP | RTqPCR | LAMP Result |
| 02 | 32.65 | 31.11 | Detected | Not Detected |
| 05 | Undetermined | 31.22 | Not Detected | Not Detected |

TABLE 7-continued

| Clinical Samples Trial VAL1-CDC 10-15 | | | | |
|---|---|---|---|---|
| Sample | 2019nCoV N1 | RP | RTqPCR | LAMP Result |
| 08 | Undetermined | 31.13 | Not Detected | Not Detected |
| 10 | 30.09 | 34.04 | Detected | Not Detected |
| 15 | Undetermined | 27.27 | Not Detected | Not Detected |
| 20 | 26.85 | 30.27 | Detected | Not Detected |
| 22 | Undetermined | 30.63 | Not Detected | Not Detected |
| 23 | 23.66 | 27.95 | Detected | Detected |
| 25 | 15.12 | 24.07 | Detected | Detected |
| 26 | 26.40 | 32.05 | Detected | partial |
| 27 | 19.84 | 33.10 | Detected | Not Detected |
| 28 | 19.65 | 39.51 | Detected | Detected |
| 30 | 24.68 | 29.95 | Detected | Detected |
| 34 | 16.27 | Undetermined | Detected | Detected |
| 36 | Undetermined | 30.48 | Not Detected | Not Detected |
| 37 | 22.66 | 42.14 | Detected | Detected |
| 38 | 28.04 | 31.71 | Detected | partial |
| 40 | 24.06 | 30.00 | Detected | Detected |
| 42 | 19.25 | Undetermined | Detected | Detected |
| 57 | 18.91 | 44.38 | Detected | Detected |
| 59 | 32.52 | 29.20 | Detected | Not Detected |
| 60 | Undetermined | 31.96 | Not Detected | Not Detected |
| 61 | 23.15 | 31.28 | Detected | Detected |
| 64 | 25.00 | 30.80 | Detected | Detected |
| 69 | 27.22 | 29.29 | Detected | Detected |
| 71 | Undetermined | Undetermined | Invalid | Not Detected |
| 75 | 8.25 | Undetermined | Detected | Detected |
| 77 | Undetermined | 27.49 | Not Detected | Not Detected |
| 82 | 24.90 | 31.39 | Detected | Detected |
| 85 | Undetermined | 29.84 | Not Detected | Not Detected |
| 86 | 25.45 | 27.67 | Detected | Detected |
| 89 | 31.67 | 24.45 | Detected | Not Detected |
| 92 | 11.39 | 42.12 | Detected | Detected |
| 93 | Undetermined | 25.92 | Not Detected | Not Detected |
| 95 | 16.38 | Undetermined | Detected | Detected |

The LAMP assay was also used to detect coronavirus in saliva samples directly, increasing the reaction volume 4 fold, with no nucleic acid extraction step. The LAMP assay was performed as above except the saliva was used directly, without extracting RNA. In some embodiments, the saliva samples can be heat inactivated for safety. Results are shown in Table 8. Sensitivity using saliva samples directly, was comparable to that of the LAMP assay using RNA extracted from the saliva samples.

5 µL of each assay was run on a 100 agarose gel to confirm specific amplification of SARS-CoV-2. By electrophoresis analysis, sample 9 was a false negative, since no SARS-CoV-2-specific amplification products were observed in the gel analysis.

TABLE 8

| Positive Saliva samples | |
|---|---|
| Sample | Ct value |
| 6 | 21.3 |
| 7 | 18.3 |
| 8 | 32.4 |
| 9 | 18 |
| 10 | 26.2 |

The invention claimed is:

1. A LAMP primer set for amplification of a SARS-CoV-related betacoronavirus target nucleic acid, comprising:
    (a) a F3 primer comprising a nucleotide sequence selected from SEQ ID NOs: 1-9;
    (b) a FIP primer comprising a nucleotide sequence selected from SEQ ID NOs: 10-18;
    (c) a B3 primer comprising the nucleotide sequence of SEQ ID NO: 20; and
    (d) a BIP primer comprising the nucleotide sequence of SEQ ID NO: 21.

2. The LAMP primer set of claim 1, wherein:
    (a) the F3 primer consists of the nucleic acid sequence of any of SEQ ID NOs: 1-9;
    (b) the FIP primer consists of the nucleic acid sequence of any of SEQ ID NOs: 10-18;
    (c) the B3 primer consists of the nucleic acid sequence of SEQ ID NO: 20; and
    (d) the BIP primer consists of the nucleic acid sequence of SEQ ID NO: 21.

3. The LAMP primer set of claim 1, wherein:
    (a) the F3 primer comprises SEQ ID NO: 1;
    (b) the FIP primer comprises SEQ ID NO: 10;
    (c) the B3 primer comprises SEQ ID NO: 20; and
    (d) the BIP primer comprises SEQ ID NO: 21.

4. The LAMP primer set of claim 1, further comprising:
    (a) a forward loop (FL) primer comprising the nucleic acid sequence of SEQ ID NO: 19; and
    (b) a backward loop (BL) primer comprising the nucleic acid sequence of SEQ ID NO: 22.

5. The LAMP primer set of claim 4, wherein:
    (a) the FL primer consists of SEQ ID NO: 19; and
    (b) the BL primer consists of SEQ ID NO: 22.

6. The LAMP primer set of claim 1, wherein one or more of the primers contains one or more modified nucleotides.

7. A kit for amplifying or detecting a SARS-CoV-related betacoronavirus, wherein the kit comprises the LAMP primer set claim 1.

8. The kit of claim 7, wherein the kit further comprises a reaction mixture comprising one or more of: dNTPs, buffer, colorimetric agent, pH-sensitive dye that changes color upon acidification, metal ion indicator, DNA polymerase, uracil DNA glycosylase, guanidine hydrochloride, helicase, a detection probe, virus inactivation agent, and RNA release agent.

9. The kit of claim 8, wherein the colorimetric agent comprises calcein, hydroxynaphthol blue, malachite green, phenol red, cresol red, neutral red, m-cresol purple, Eva green, or N',N'-dimethyl-N-[4-[(E)-(3-methyl-1,3-benzothiazol-2-ylidene)methyl]-1-phenylquinolin-1-ium-2-yl]-N-propylpropane-1,3-diamine.

10. The kit of claim 8, wherein the DNA polymerase comprises a thermostable strand displacing reverse transcriptase.

11. The kit of claim 10, wherein the thermostable strand displacing reverse transcriptase comprises a *Bacillus stearothermophilus* (Bst) DNA polymerase, a modified Bst DNA polymerase, or a Bst DNA Polymerase having a reversibly-bound aptamer that inhibits polymerase activity at temperatures below 45° C.

12. The kit of claim 8, wherein the uracil DNA glycosylase comprises an Antarctic thermolabile uracil DNA glycosylase.

13. The kit of claim 8, wherein the kit further comprises 40±20 mM, 40±15 mM, 40±10 mM, or 40±5 mM guanidine hydrochloride.

14. The kit of claim 8, wherein the kit further comprises one or more of: (a) a positive control test sample containing a betacoronavirus target nucleic acid sequence; (b) a negative control test sample that does not contain a betacoronavirus target nucleic acid; (c) a housekeeping gene control sample that contains a primer set designed to amplify a housekeeping gene nucleic acid sequence; and (d) instructions for use or a notice in a form prescribed by a governmental agency regulating the manufacture, use or sale of the products.

15. A method of amplifying or detecting a SARS-CoV-related betacoronavirus in a sample, comprising performing a loop-mediated isothermal amplification reaction on the sample using the kit of claim 7, wherein the SARS-CoV-related betacoronavirus target nucleic acid, if present in the sample, is used as template for generating an amplification product, and detecting the presence or absence of the amplification product by observing a color or turbidity change.

16. The method of claim 15, wherein the sample is a clinical sample obtained from a subject.

17. The method of claim 15, wherein the sample comprises a saliva sample or RNA extracted from saliva.

18. A method of diagnosing SARS-CoV-2 infection in a subject, comprising: performing a loop-mediated isothermal amplification reaction on the sample using the kit of claim 7, wherein the SARS-CoV-2 target nucleic acid, if present in the sample, is used as template for generating an amplification product; and detecting the presence or absence of the amplification product, wherein detecting the presence of the amplification product indicates SARS-CoV-2.

* * * * *